United States Patent
Ding et al.

(10) Patent No.: US 10,359,383 B2
(45) Date of Patent: Jul. 23, 2019

(54) METHOD OF DETECTING GALVANIC INSULATION INTEGRITY

(71) Applicant: United Technologies Corporation, Farmington, CT (US)

(72) Inventors: Zhongfen Ding, South Windsor, CT (US); Mark R. Jaworowski, Glastonbury, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 405 days.

(21) Appl. No.: 15/174,092

(22) Filed: Jun. 6, 2016

(65) Prior Publication Data
US 2017/0350840 A1    Dec. 7, 2017

(51) Int. Cl.
G01R 31/36 (2019.01)
G01N 27/14 (2006.01)
G01N 17/02 (2006.01)

(52) U.S. Cl.
CPC ............ *G01N 27/14* (2013.01); *G01N 17/02* (2013.01)

(58) Field of Classification Search
CPC .............. G01R 31/025; G01R 31/3662; G01R 27/025; G01R 31/389; G01R 31/392; H01M 10/48
See application file for complete search history.

(56) References Cited

U.S. PATENT DOCUMENTS

| 4,478,915 | A  | * | 10/1984 | Poss ..................... B32B 15/08 428/607 |
| 5,126,654 | A  |   | 6/1992  | Murphy et al. |
| 8,408,229 | B2 | * | 4/2013  | Goldberg ............. A01G 25/167 137/78.3 |
| 2003/0080761 | A1 | * | 5/2003 | Filippi, Jr. ............. H01L 22/34 324/719 |
| 2014/0347071 | A1 |   | 11/2014 | Montanari et al. |

FOREIGN PATENT DOCUMENTS

EP    2474823 A1    7/2012

OTHER PUBLICATIONS

European Search Report for application EP 17174424.6, dated Sep. 27, 2017, 6 pages.

* cited by examiner

*Primary Examiner* — Alesa Allgood
(74) *Attorney, Agent, or Firm* — Cantor Colburn LLP (57) ABSTRACT

A method of assessing galvanic electronic isolation of two components at a joint of the two components includes measuring a first electrical resistance at a first condition across a joint of two components and comparing the first electrical resistance to a threshold resistance. The comparison of the first electrical resistance to the threshold resistance is indicative of a degree of electrical isolation of the two components. A second electrical resistance is measured at a second condition and the second electrical resistance is compared to the first electrical resistance. The result of the comparison of the second electrical resistance to the first electrical resistance is indicative of a type of electrical connection between the two components.

18 Claims, 6 Drawing Sheets

METHOD OF DETECTING GALVANIC INSULATION INTEGRITY

BACKGROUND

This disclosure relates to metallic components, and more particularly to the detection of the integrity of a dielectric insulation layer located between dissimilar metals of a metallic component.

Many industrial components are formed from metals, and often results in joints where dissimilar metals are joined. Normally, a dielectric insulation layer is located between a first dissimilar metal and a second dissimilar metal at the joint to prevent potentially damaging galvanic corrosion at the dissimilar metal joint. Damage to or loss of integrity of the dielectric insulation can result in an electrical connection between the two metals, leading to galvanic corrosion.

In addition to detecting a true electrical connection between the two dissimilar metals that would lead to galvanic corrosion, it is desired to distinguish between the true electrical connection and an ionic conduction condition that will not result in galvanic corrosion.

SUMMARY

In one embodiment, a method of assessing galvanic electronic isolation of two components at a joint of the two components includes measuring a first electrical resistance at a first condition across a joint of two components and comparing the first electrical resistance to a threshold resistance. The comparison of the first electrical resistance to the threshold resistance is indicative of a degree of electrical isolation of the two components. A second electrical resistance is measured at a second condition and the second electrical resistance is compared to the first electrical resistance. The result of the comparison of the second electrical resistance to the first electrical resistance is indicative of a type of electrical connection between the two components.

Additionally or alternatively, in this or other embodiments the first electrical resistance is measured at a first temperature, and the second electrical resistance is measured at a second temperature.

Additionally or alternatively, in this or other embodiments the second temperature is greater than the first temperature.

Additionally or alternatively, in this or other embodiments the second temperature is at least 10 degrees Celsius greater than the first temperature.

Additionally or alternatively, in this or other embodiments the joint is heated to the second temperature.

Additionally or alternatively, in this or other embodiments the joint is heated via one of an oven, or a heat gun, or some other heating device such as a laser beam.

Additionally or alternatively, in this or other embodiments if the second electrical resistance is greater than the first electrical resistance, the comparison of the second electrical resistance to the first electrical resistance is indicative of a galvanic electronic connection between the two components.

Additionally or alternatively, in this or other embodiments if the first electrical resistance is greater than the second electrical resistance, the comparison of the second electrical resistance to the first electrical resistance is indicative of an ionic conduction condition across the joint.

Additionally or alternatively, in this or other embodiments the first electrical resistance is measured at a first polarity, and the second electrical resistance is measured at a second polarity.

Additionally or alternatively, in this or other embodiments the first electrical resistance is measured at a first electrical voltage V1, and the second electrical resistance is measured at a second electrical voltage V2.

Additionally or alternatively, in this or other embodiments the first electrical resistance is measured at a first lower frequency, and the second electrical resistance is measured at a second higher frequency.

Additionally or alternatively, in this or other embodiments a difference between the first electrical resistance and the second electrical resistance is indicative of an ionic conduction condition across the joint.

Additionally or alternatively, in this or other embodiments a second electrical resistance equal to the first electrical resistance is indicative of a galvanic electronic connection between the two components.

Additionally or alternatively, in this or other embodiments a first electrical resistance equal to or greater than the threshold resistance is indicative of a desired electrical isolation of the two components.

Additionally or alternatively, in this or other embodiments a first component of two components is formed from a first metal and a second component of the two components is formed from a second metal different than the first metal.

In another embodiment, a system for assessing electrical isolation of two components at a joint of the two components includes a resistance measuring device electrically connected to the two components, and an evaluation device connected to the resistance measuring device and configured to compare a first electrical resistance measured at a first condition to a threshold resistance. The comparison of the first electrical resistance to the threshold resistance is indicative of a degree of electrical isolation of the two components. The evaluation device is configured to compare a second electrical resistance measured at a second condition to the first electrical resistance. The result of the comparison of the second electrical resistance to the first electrical resistance is indicative of a type of electrical connection between the two components.

Additionally or alternatively, in this or other embodiments the first electrical resistance is measured at a first temperature and the second electrical resistance is measured at a second temperature greater than the first temperature.

Additionally or alternatively, in this or other embodiments an oven and/or a heat gun or some other heating method is utilized to heat the joint to the second temperature.

Additionally or alternatively, in this or other embodiments if the second electrical resistance is greater than the first electrical resistance, the comparison of the second electrical resistance to the first electrical resistance is indicative of a galvanic electronic connection between the two components.

Additionally or alternatively, in this or other embodiments if the first electrical resistance is greater than the second electrical resistance, the comparison of the second electrical resistance to the first electrical resistance is indicative of an ionic conduction condition across the joint.

Additionally or alternatively, in this or other embodiments the first electrical resistance is measured at a first polarity, and the second electrical resistance is measured at a second polarity.

Additionally or alternatively, in this or other embodiments the first electrical resistance is measured at a first electrical voltage V1, and the second electrical resistance is measured at a second electrical voltage V2.

Additionally or alternatively, in this or other embodiments the first electrical resistance/impedance is measured at a first lower frequency, and the second electrical resistance/impedance is measured at a second higher frequency.

Additionally or alternatively, in this or other embodiments a difference between the first electrical resistance and the second electrical resistance is indicative of an ionic conduction condition across the joint, and a second electrical resistance equal to the first electrical resistance is indicative of a galvanic electronic connection between the two components.

BRIEF DESCRIPTION OF THE DRAWINGS

The subject matter which is regarded as the present disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
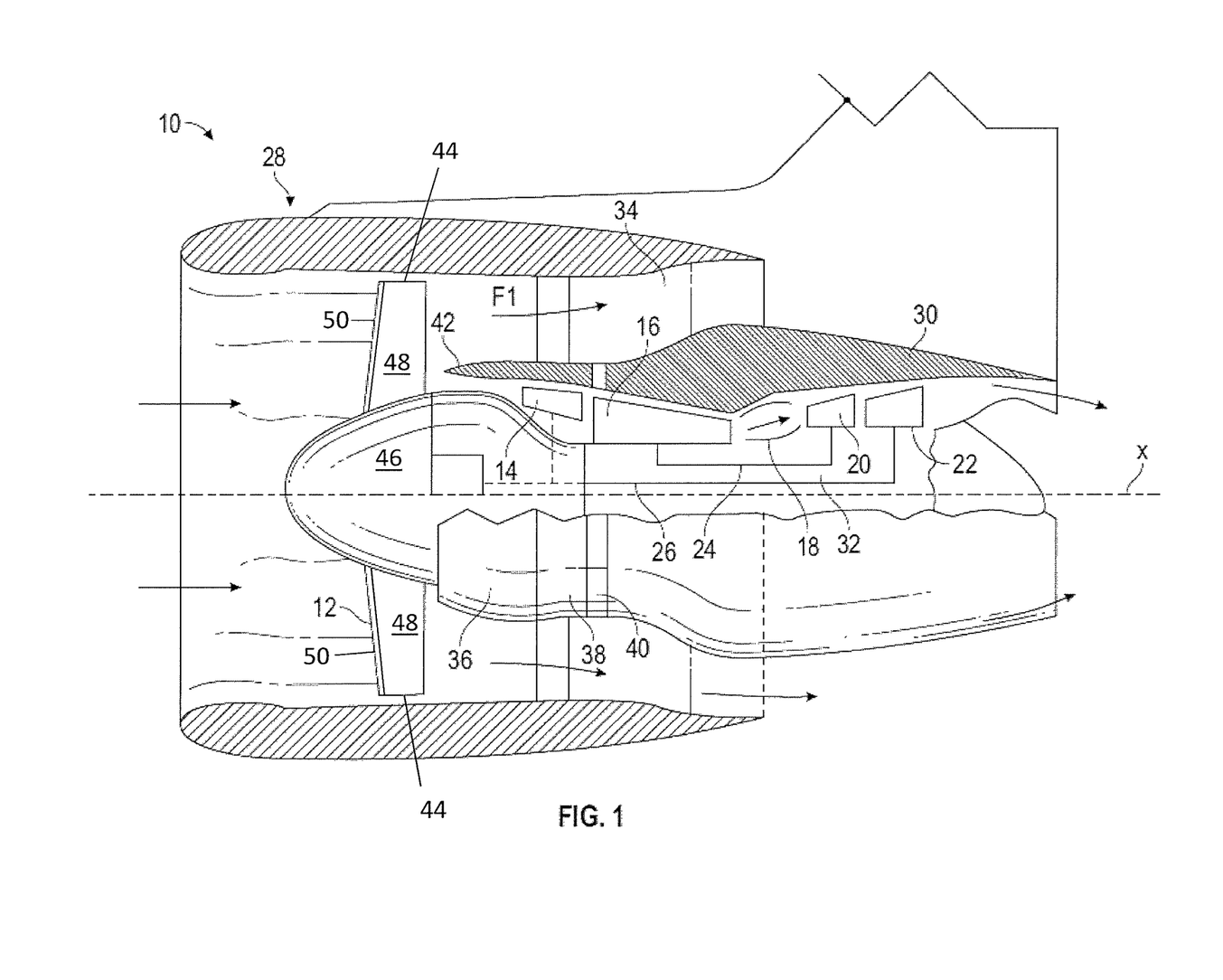
FIG. 1 illustrates a cross-sectional view of an embodiment of a gas turbine engine.

FIG. 1 is a schematic illustration of a gas turbine engine 10. The gas turbine engine generally has includes fan section 12, a low pressure compressor 14, a high pressure compressor 16, a combustor 18, a high pressure turbine 20 and a low pressure turbine 22. The gas turbine engine 10 is circumferentially disposed about an engine centerline X. During operation, air is pulled into the gas turbine engine 10 by the fan section 12, pressurized by the compressors 14, 16, mixed with fuel and burned in the combustor 18. Hot combustion gases generated within the combustor 18 flow through high and low pressure turbines 20, 22, which extract energy from the hot combustion gases.

In a two-spool configuration, the high pressure turbine 20 utilizes the extracted energy from the hot combustion gases to power the high pressure compressor 16 through a high speed shaft 24, and the low pressure turbine 22 utilizes the energy extracted from the hot combustion gases to power the low pressure compressor 14 and the fan section 12 through a low speed shaft 26. The present disclosure, however, is not limited to the two-spool configuration described and may be utilized with other configurations, such as single-spool or three-spool configurations, or gear-driven fan configurations.

Gas turbine engine 10 is in the form of a high bypass ratio turbine engine mounted within a nacelle or fan casing 28 which surrounds an engine casing 30 housing an engine core 32. A significant amount of air pressurized by the fan section 12 bypasses the engine core 32 for the generation of propulsive thrust. The airflow entering the fan section 12 may bypass the engine core 32 via a fan bypass passage 34 extending between the fan casing 28 and the engine casing 30 for receiving and communicating a discharge flow F1. The high bypass flow arrangement provides a significant amount of thrust for powering an aircraft.

The engine casing 30 generally includes an inlet case 36, a low pressure compressor case 38, and an intermediate case 40. The inlet case 36 guides air to the low pressure compressor case 38, and via a splitter 42 also directs air through the fan bypass passage 34.

The fan section 12 includes a plurality of fan blades 44 extending radially outwardly from a hub 46. The fan blade 44 includes an airfoil body 48 formed from a first metal, for example, an aluminum alloy. A leading edge portion 50 is joined to the airfoil body 48 and is formed from a second metal, for example, a titanium alloy to improve erosion and impact resistance of the fan blade 44. While the description herein is in the context of a fan blade 44, one skilled in the art will readily appreciate that the apparatus and method described herein may be utilized with a wide array of joints between components formed from dissimilar metals.

Figure 2:
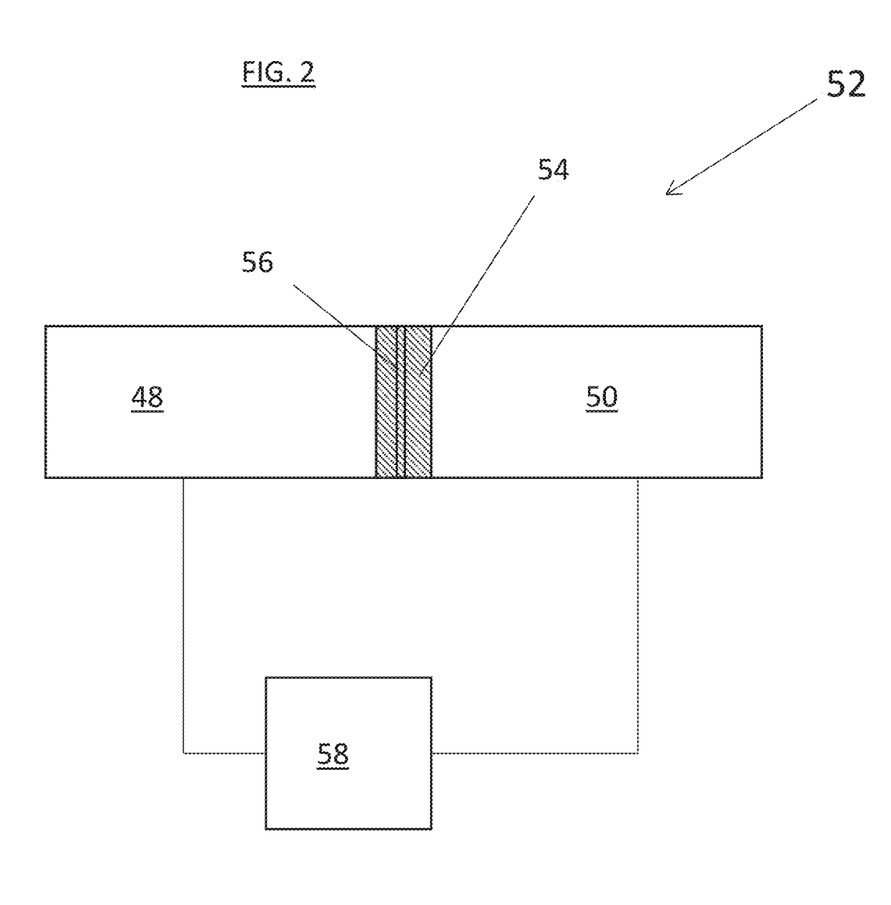
FIG. 2 illustrates a schematic cross-sectional view of an embodiment of a joint between two dissimilar metal components.

Shown in FIG. 2 is a cross-sectional view of such a joint. In the joint 52, a first component, for example, airfoil body 48 formed from a first metal is joined to a second component, for example, leading edge portion 50, formed from a second metal, dissimilar to the first metal. In some embodiments, the airfoil body 48 is joined to the leading edge portion 50 by an adhesive layer 54 located between the airfoil body 48 and the leading edge portion 50. In some embodiments, the adhesive layer 54 also acts as a dielectric insulator between the airfoil body 48 and the leading edge portion 50, while in other embodiments such as shown in FIG. 2 a separate dielectric insulation layer 56 is located between the airfoil body 48 and the leading edge portion 50.

It is desired to check the integrity of the dielectric insulation layer 56 between the airfoil body 48 and the leading edge portion 50 ensuring there is no electrical connection between the airfoil body 48 and the leading edge portion 50, which would lead to galvanic corrosion of the airfoil body 48 and/or the leading edge portion 50. Further, the check would need to distinguish between a true electrical connection and an ionic conduction condition due to the presence of, for example, an electrolytic film at the joint 52. In some embodiments, the check occurs as part of the manufacturing process while in other embodiments, the check may be performed periodically during the service life of the airfoil body 48 and the leading edge portion 50 to ensure continued integrity of the dielectric insulation layer 56.

In an embodiment, a multimeter 58 or other similar tool for resistance (or impedance) measurement is connected to the airfoil body 48 and the leading edge portion 50 and is utilized to measure an electrical resistance (or impedance) across the joint 52, and by utilizing the method described below will distinguish between a true electrical connection between the airfoil body 48 and the leading edge portion 50, which will result in galvanic corrosion, and ionic conduction across the joint 52.

Figure 3:
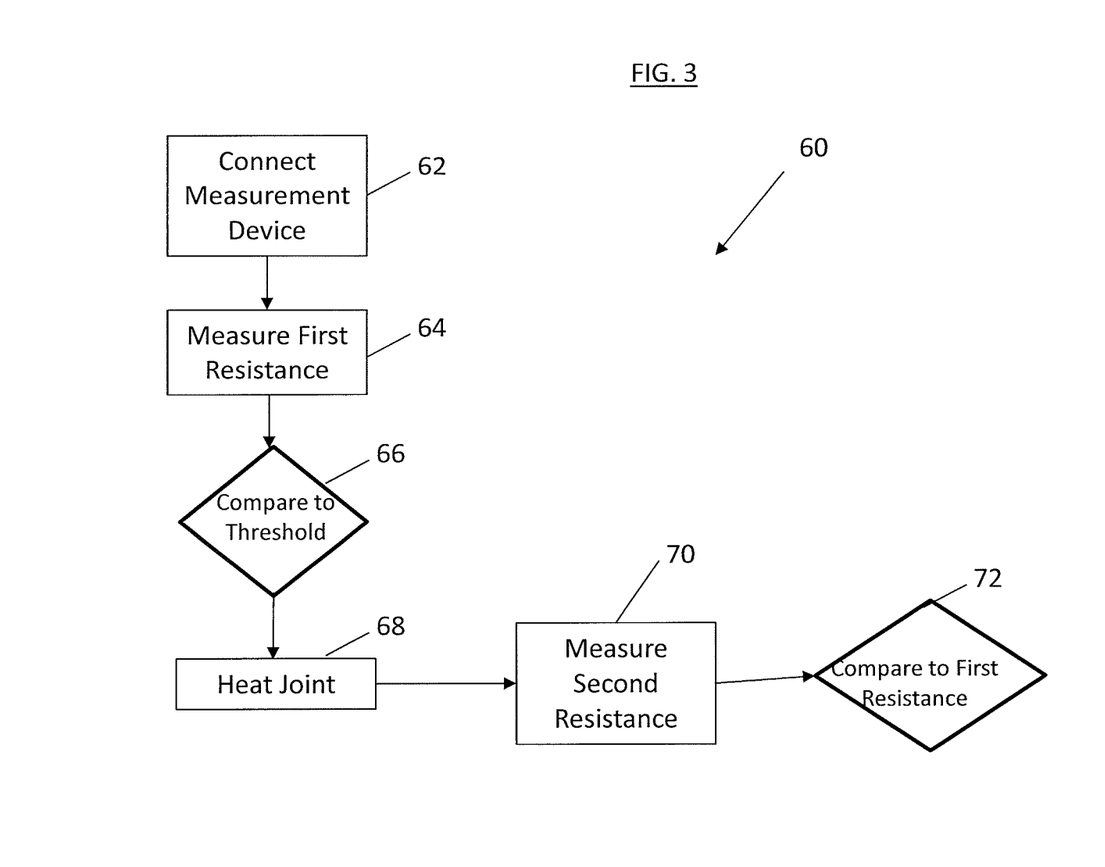
FIG. 3 is a schematic illustration of a method for assessing galvanic isolation of a joint between a first component and a second component.

Referring now to FIG. 3, in one embodiment, the method 60 includes connecting the multimeter 58 to the airfoil body 48 and the leading edge portion 50 at block 62, and measuring a first resistance across the joint 52 at block 64. In some embodiments, the first resistance is measured while the joint 52 is at room temperature, or in ambient conditions. The first resistance is compared to a threshold resistance at block 66, at an evaluation device. In some embodiments, the threshold resistance is about one giga-Ohm or $1\times10^9$ Ohms. A measurement of the first resistance equal to or greater than the threshold is indicative of the airfoil body 48 and the leading edge portion 50 having a selected degree of electrical isolation from each other.

If the measured first resistance is less than the threshold resistance the airfoil body 48 and the leading edge portion 50 have a degree of electrical connection therebetween, and further method steps will determine whether the electrical connection is one of ionic conduction, which will not result in galvanic corrosion, or a true electrical connection which will result in galvanic corrosion.

In block 68, the joint 52 is heated to an elevated temperature greater than a baseline temperature at which the first resistance was measured. In some embodiments, the joint 52 is heated by placing the airfoil body 48 and the leading edge portion 50 in an oven or alternatively applying a heat gun to the joint 52. In some embodiments, the elevated temperature is at least 10° Celsius greater than the baseline temperature. A second resistance is measured while the joint 52 is at the elevated temperature at block 70 and the second resistance is compared to the first resistance at block 72.

The electrical resistance of metals has a positive temperature coefficient, i.e., the electrical resistance increases with an increase in temperature. For example, aluminum has a positive electrical resistance temperature coefficient of about $4.3\times10^{-3}$. With a temperature increase of 10° Celsius, the electrical resistance will increase by about 4.3%. Conversely, resistance due to ionic conduction has a negative temperature coefficient. In ionic conduction, as the temperature increases the ions will move faster and the electrical resistance will decrease. The negative temperature coefficient depends on the specific ionic system, but it is more significant than for metals, on the order of about $-20\times10^{-3}$. Restated, for a temperature increase of 10° Celsius, the ionic resistance will decrease by about 20%. Thus, the result of the comparison between the first measured resistance and the second measured resistance will indicate whether ionic conduction or a true electronic connection is present.

If the comparison at block 72 indicates the second measured resistance is greater than the first measured resistance, a true electronic connection resulting in galvanic corrosion is present, while if the comparison at block 72 indicates the second measured resistance is less than the first measured resistance, ionic conduction is present.

Figure 4:
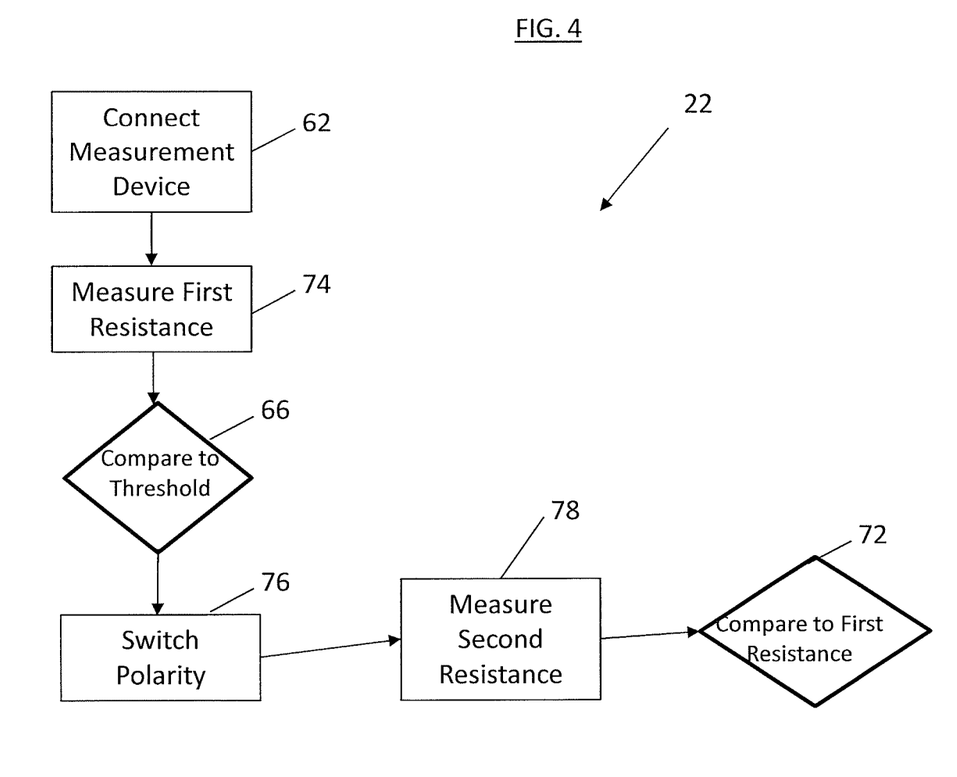
FIG. 4 is a schematic illustration of another method for assessing galvanic isolation of a joint between a first component and a second component.

In another embodiment, as illustrated in FIG. 4, the first resistance is measured at a first polarity 74, and the leads connected to the airfoil body 48 and the leading edge portion 50 are switched at block 76, reversing the polarity. The second resistance is measured at block 78 at the reversed polarity. The first resistance is compared to the second resistance at block 80, with no difference between the first resistance and the second resistance indicative of a true electronic connection leading to galvanic corrosion, while if the first resistance is different from the second resistance, the result of the comparison is indicative of ionic conduction and not a true electronic connection.

Figure 5:
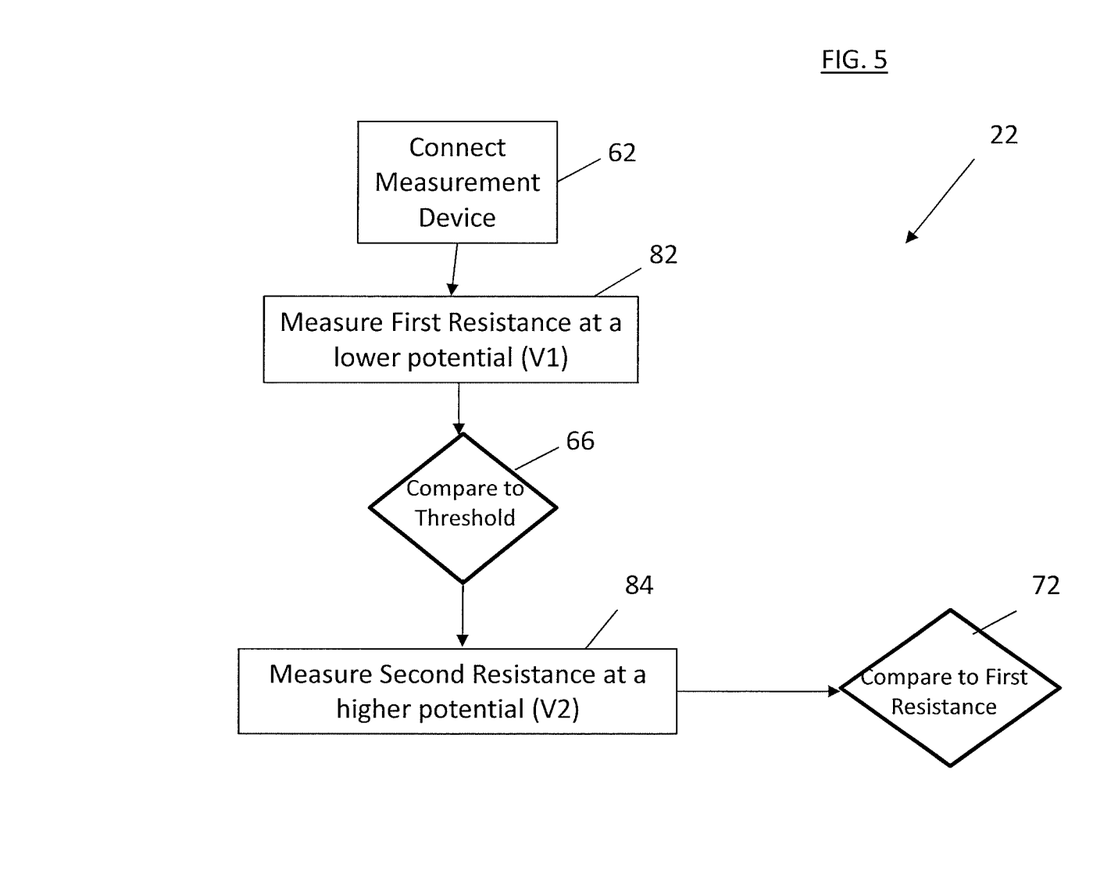
FIG. 5 is a schematic illustration of a third method for assessing galvanic isolation of a joint between a first component and a second component.

In another embodiment, as illustrated in FIG. 5, the first resistance is measured at a first lower potential (V1) 82 while the second resistance is measured at a higher potential (V2) 84. The potential at which the first resistance and the second resistance is measured may be varied, with a difference in the measured resistances indicative of ionic conduction, while when the measured resistance is constant the result is indicative of a true electronic connection leading to galvanic corrosion.

Figure 6:
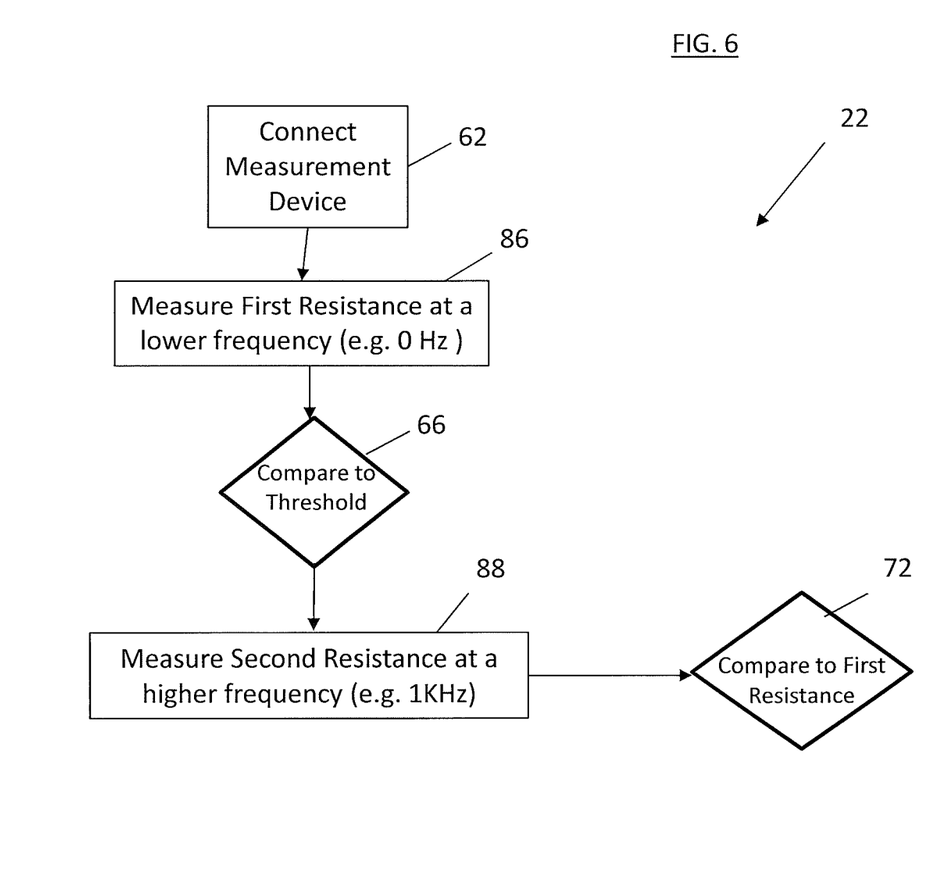
FIG. 6 is a schematic illustration of a fourth method for assessing galvanic isolation of a joint between a first component and a second component.

In another embodiment, as illustrated in FIG. 6, the first resistance is measured at a lower frequency (for example, 0 Hz direct current) 86 while the second resistance is measured at a higher frequency (for example, at 1 KHz) 88. The frequency at which the first resistance and the second resistance is measured may be varied, with a difference in the measured resistances indicative of ionic conduction, while when the measured resistance is constant the result is indicative of a true electronic connection leading to galvanic corrosion.

The methods presented in the present disclosure are straightforward and practical, requiring a minimum amount of additional equipment such that the methods may be performed reliably in, for example, a manufacturing or service facility.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

The invention claimed is:

1. A method of assessing galvanic electronic isolation of two components at a joint of the two components, comprising: connecting an electrical resistance measurement tool to a first component of the two components and to a second component of the two components; measuring a first electrical resistance at a first condition across a joint of the two components using the electrical resistance measurement tool; comparing the first electrical resistance to a threshold resistance, the comparison of the first electrical resistance to the threshold resistance indicative of a degree of electrical isolation of the two components; measuring a second electrical resistance at a second condition using the electrical resistance measurement tool; comparing the second electrical resistance to the first electrical resistance, the result of the comparison of the second electrical resistance to the first electrical resistance indicative of a type of electrical connection between the two components; and determining whether the type of electrical connection is ionic conduction or is a galvanic connection via the comparison of the second electrical resistance to the first electrical resistance; wherein a first component of two components is formed from a first material and a second component of the two components is formed from a second material different than the first material, wherein the first electrical resistance is measured at a first temperature; and the second electrical resistance is measured at a second temperature different from the first temperature.

2. The method of claim 1, wherein a first electrical resistance equal to or greater than the threshold resistance is indicative of a desired electrical isolation of the two components.

3. The method of claim 1, wherein the second temperature is at least 10 degrees Celsius greater than the first temperature.

4. The method of claim 3, wherein the joint is heated to the second temperature.

5. The method of claim 3, wherein if the second electrical resistance is greater than the first electrical resistance, the comparison of the second electrical resistance to the first electrical resistance is indicative of a galvanic electronic connection between the two components.

6. The method of claim 3, wherein if the first electrical resistance is greater than the second electrical resistance, the comparison of the second electrical resistance to the first electrical resistance is indicative of an ionic conduction condition across the joint.

7. The method of claim 1, further comprising: measuring the first electrical resistance at a first polarity; and measuring the second electrical resistance at a second polarity different from the first polarity.

8. The method of claim 7, wherein a difference between the first electrical resistance and the second electrical resistance is indicative of an ionic conduction condition across the joint.

9. The method of claim 7, wherein a second electrical resistance equal to the first electrical resistance is indicative of a galvanic electronic connection between the two components.

10. A system for assessing electrical isolation of two components at a joint of the two components, comprising: a resistance measuring device electrically connected to the two components; and an evaluation device connected to the resistance measuring device and configured to: compare a first electrical resistance measured at a first condition to a threshold resistance, the comparison of the first electrical resistance to the threshold resistance indicative of a degree of electrical isolation of the two components; compare a second electrical resistance measured at a second condition to the first electrical resistance, the result of the comparison of the second electrical resistance to the first electrical resistance indicative of a type of electrical connection between the two components; and determining whether the type of electrical connection is ionic conduction or is a galvanic connection via the comparison of the second electrical resistance to the first electrical resistance; wherein a first component of two components is formed from a first material and a second component of the two components is formed from a second material different than the first material, and a joint between the first component and the second component is defined by an adhesive layer disposed between the first component and the second component; where the first electrical resistance is measured at a first temperature; and the second electrical resistance is measured at a second temperature greater than the first temperature.

11. The system of claim 10, wherein if the second electrical resistance is greater than the first electrical resistance, the comparison of the second electrical resistance to the first electrical resistance is indicative of a galvanic electronic connection between the two components.

12. The system of claim 10, wherein if the first electrical resistance is greater than the second electrical resistance, the comparison of the second electrical resistance to the first electrical resistance is indicative of an ionic conduction condition across the joint.

13. The system of claim 10, wherein: the first electrical resistance is measured at a first polarity; and the second electrical resistance is measured at a second polarity different from the first polarity.

14. The system of claim 13, wherein:
a difference between the first electrical resistance and the second electrical resistance is indicative of an ionic conduction condition across the joint; and
a second electrical resistance equal to the first electrical resistance is indicative of a galvanic electronic connection between the two components.

15. The system of claim 10, wherein:
the first electrical resistance is measured at a first electrical voltage; and
the second electrical resistance is measured at a second electrical voltage that is different from the first electrical voltage.

16. The system of claim 15, wherein:
a difference between the first electrical resistance and the second electrical resistance is indicative of an ionic conduction condition across the joint; and
a second electrical resistance equal to the first electrical resistance is indicative of a galvanic electronic connection between the two components.

17. The system of claim 10, wherein:
the first electrical resistance is measured at a first lower frequency; and
the second electrical resistance is measured at a second higher frequency.

18. The system of claim 17, wherein:
a difference between the first electrical resistance and the second electrical resistance is indicative of an ionic conduction condition across the joint; and
a second electrical resistance equal to the first electrical resistance is indicative of a galvanic electronic connection between the two components.

* * * * *